US006224886B1

(12) United States Patent
Charlton et al.

(10) Patent No.: US 6,224,886 B1
(45) Date of Patent: May 1, 2001

(54) SKIN WASH COMPOSITIONS COMPRISING TRICLOCARBAN AND SURFACTANTS

(75) Inventors: Lynda Rosemary Charlton, Staines; Juliet Teresa McGillycuddy, Bracknell, both of (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/202,441

(22) PCT Filed: Jun. 10, 1997

(86) PCT No.: PCT/EP97/03055

§ 371 Date: Dec. 15, 1998

§ 102(e) Date: Dec. 15, 1998

(87) PCT Pub. No.: WO97/48377

PCT Pub. Date: Dec. 24, 1997

(30) Foreign Application Priority Data

Jun. 15, 1996 (GB) .................................................. 9612595

(51) Int. Cl.⁷ .............................. A61K 6/00; A61K 7/00; A61K 31/74; A01N 25/34
(52) U.S. Cl. ...................... 424/401; 424/78.03; 424/404
(58) Field of Search ................................... 252/106, 117, 252/132; 424/78.03, 401, 404

(56) References Cited

U.S. PATENT DOCUMENTS 5,264,145 * 11/1993 French et al. ........................ 252/117
5,395,542 * 3/1995 Nozaki et al. ................... 252/174.16

FOREIGN PATENT DOCUMENTS 0 422 508   4/1991  (EP) .
0 670 158   9/1995  (EP) .
WO 92 18100  10/1992  (WO) .
WO 97 03648  2/1997  (WO) .

OTHER PUBLICATIONS

Derwent Publications Ltd. AN 90–222290, London, GB, Jun. 12, 1990, See abstract JP02152920.

* cited by examiner

Primary Examiner—Thurman K. Page
Assistant Examiner—S. Howard
(74) Attorney, Agent, or Firm—Nora Stein-Fernandez; Stephen Venetianer; Charles M. Kinzig

(57) ABSTRACT

The compositions of the present invention are useful for the topical delivery of a wide variety of active ingredients. These compositions are particularly useful for treating conditions such as acne and its attendant skin lesions, blemishes, and other imperfections. These compositions are nonirritating to the skin and also provide skin feel benefits. These compositions can be in the form of leave-on products and products that are rinsed or wiped from the skin after use.

16 Claims, 1 Drawing Sheet

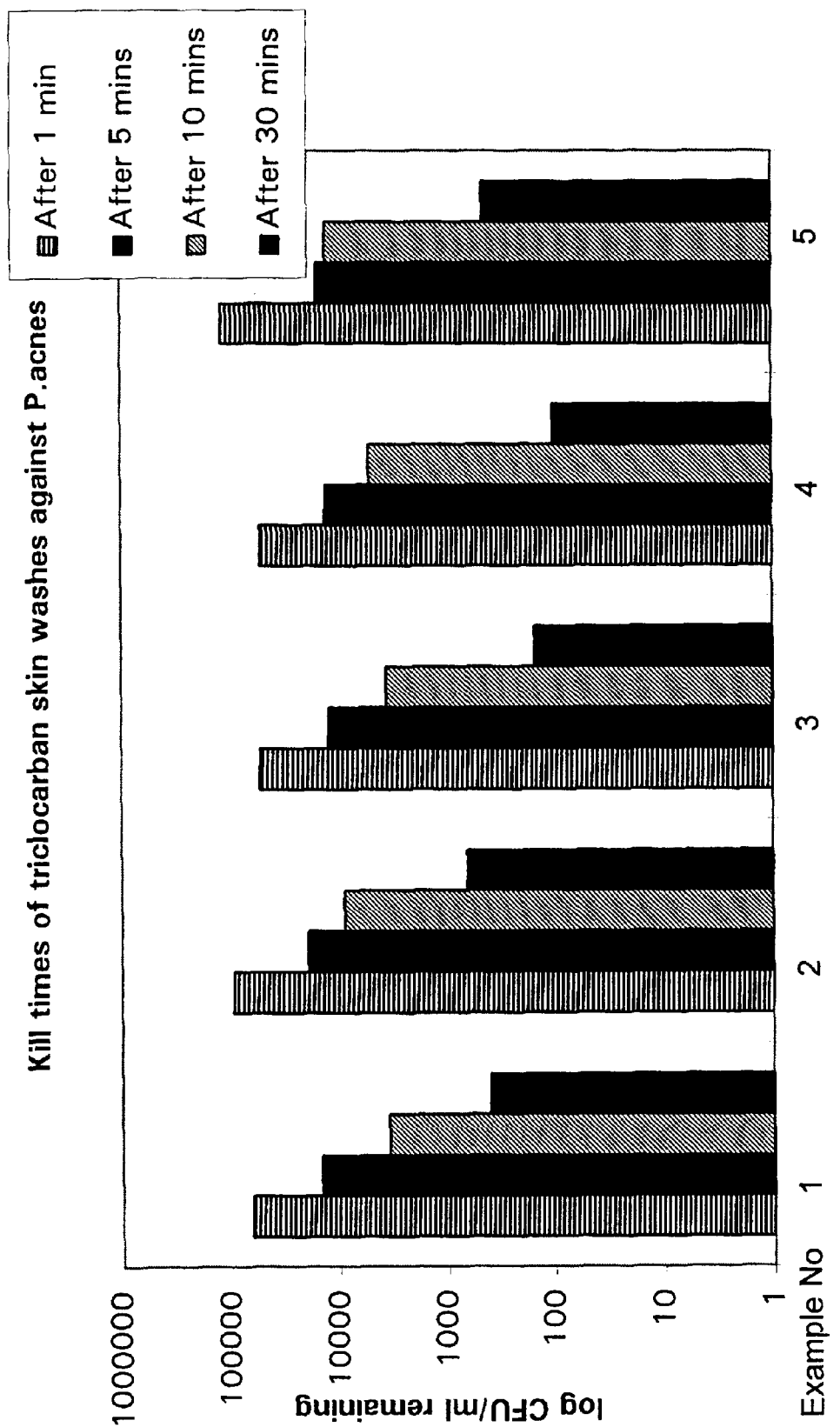

SKIN WASH COMPOSITIONS COMPRISING TRICLOCARBAN AND SURFACTANTS

The present invention relates to compositions for topical application to the skin surface including the scalp, in particular to antibacterial skin wash compositions which are applied to water-wetted skin, and subsequently rinsed off with water. Specifically, the present invention relates to skin wash compositions comprising triclocarban as the active antibacterial ingredient formulated in a mild and non-irritant detergent base.

Antibacterial cleansing compositions are widely used in the health care industry, for example in hospitals, in the form of scrubs and washes. Skin cleansing compositions comprising an antibacterial agent also have utility in the domestic environment both as general cleansers and in particular for the treatment and prevention of acne, a pilosebaceous disease characterised by comedones containing sebum, protein debris and anaerobic microorganisms including *Propionibacterium acnes* (*P. acnes*). The active ingredient of products which are currently available on general sale as skin cleansers, including cleansers targeted for the treatment and prevention of acne, include for example salicylic acid, benzoyl peroxide and triclosan. Such compounds whilst conferring a beneficial effect on the skin may cause local irritation when applied to sensitive areas, in particular the face. Moreover, local irritation may be exacerbated by the carrier system in which the active ingredient is formulated. For example, skin wash compositions and in particular face wash compositions which generally include a soap-free detergent base selected for effective cleansing and foaming, may confer an irritant effect due to the use of surfactants commonly employed in such detergent systems.

European Patent Publication 0 670 158 A2 discloses an aqueous liquid composition comprising about 4 to 10 wt % of anionic surfactant about 1.5 to 5 wt % of betaine about 1.5 to 8 wt % of an alkyl polyglycoside wherein the average degree of polymerisation is from about 1.1 to 6 and the average alkyl length is from about 8 to 16 carbon atoms inclusive, and an antibacterial effective amount of an antibacterial agent or mixture of antibacterial agents, which compositions are described as being at least as mild if not actually milder than various commercial antibacterial liquid cleansing compositions on the market place. The preferred antibacterial agent is a member of the family of halogenated phenoxy diphenyl ethers, most preferably the compound 2,4,4'-trichloro-2'-hydroxyphenylether which has the generic name triclosan.

Triclocarban (3,4,4'-trichlorocarbanilide-N-(4-chloropheny-N-3,4-dichlorophenyl)urea) is an antibacterial agent with broad spectrum activity. It is effective against bacteria commonly found on the skin, including pathogenic Staphylococcus species which are resistant to many bacteriostats. It has been shown to reduce body odour by preventing growth of the causative organisms. It is non-irritant and has a high affinity for the skin which means that the bacteriostatic effect persists after application. The low mammalian toxicity of triclocarban together with its antibacterial activity have given rise to its usage as a bacteriostatic agent in bar soaps for over 35 years and more recently in liquid soap products. Triclocarban is described in the promotional materials of its commercial suppliers as having activity at low concentrations in finished products, typically in the range 0.5 to 1.5% w/w.

Triclocarban has a very low water solubility (<0.1%). This confers the advantage that once applied to the skin, it is not readily removed by rinsing. However, a problem arising from its low water solubility is that it requires addition of substantial quantities of organic solvents if a clear liquid product is to be obtained. Alternatively, it can be formulated as a suspension, the stability of which can be controlled by emulsification.

Experiments have now shown that triclocarban is highly effective against *Propionibacterium acnes* at low concentrations. The NIC value against *P. acnes* has been measured at 1.49 compared to a value of greater than 12.79 for triclosan.

It is an object of the present invention to provide a skin wash composition, preferably as a clear liquid product, containing an antibacterial agent which is effective against *P. acnes* in a detergent base which has good cleansing and foaming characteristics, which composition is mild and non-irritant to the skin. This object is achieved according to the present invention which is based on the unexpected finding that the antimicrobial agent triclocarban is effective against *P. acnes* at unusually low concentrations and can be incorporated in a mild detergent base comprising a mixture of a non-ionic alkylpolyglucoside surfactant and an amphoteric surfactant which has the desired cleansing and foaming characteristics in the absence of an anionic surfactant.

According to the present invention there is provided a skin wash composition comprising from 0.05 to 0.25% w/w of triclocarban and a detergent base consisting of a mixture of a non-ionic alkylpolyglucoside surfactant and an amphoteric surfactant in the absence of an anionic surfactant. Preferably the concentration of triclocarban in the composition will be in the range 0.075 to 0.15% w/w and more preferably 0.10% w/w. Surprisingly, it has also been found that triclocarban is more effective against *P. acnes* when the detergent base content of the composition is reduced.

As used herein, the term alkylpolyglucoside surfactant means a non-ionic surfactant derived from common natural organic monomer units as found in starch, fats and sugars, and most suitably derived from D-glucose monomer units. Alkylpolyglucosides derived from D-glucose are acetal compounds in which the alkyl residue has a carbon chain length of from 8 to 16 carbon atoms and the degree of glucosidation (or polymerisation), ie. the average number of glucose units per alkyl radical, is between 1.1 and 6. A range of suitable alkylpolyglucosides are commercially available either individually or as mixtures or blends. Compositions according to this invention will generally contain mixtures or blends of different alkylpolyglucosides. Preferred alkylpolyglucosides for use in the present invention include decyl glucoside and lauryl glucoside and mixtures thereof. Alkylpolyglucoside surfactants generally comprise up to 15% w/w of the skin wash composition, suitably from 2.0 to 10.0% w/w and preferably from 4.0 to 6.0% w/w of the composition. It will be appreciated that the amount of alkylpolyglucoside will be determined to some extent by the nature and amount of amphoteric surfactant present in the composition.

In principle, any amphoteric surfactant which is acceptable for topical application to the skin may contribute, with the alkylpolyglucoside surfactant, to the detergent base but, in view of their inherent mildness and good foaming performance, the preferred amphoteric surfactant will belong to the class of compounds known as betaines. Structurally, betaine compounds contain a carboxylate functional group and a quaternary nitrogen function separated by a methylene moiety. They include n-alkyl betaines such as cetyl betaine and behenyl betaine, and n-alkylamido betaines such as cocomidopropyl betaine. The amphoteric surfactant component of the detergent base for compositions of the present invention may be a single compound or a mixture or blend of two or more different substances. A preferred amphoteric surfactant is cocamidopropyl betaine. Amphoteric surfactants will generally comprise up to 10% w/w of the skin wash composition, suitably from 2.0 to 8.0% w/w and preferably from 2.5 to 5.0% w/w of the skin wash composition. The amount of amphoteric surfactant will to some extent be determined by the alkylpolyglucoside surfactant component of the detergent base.

Typically, the detergent base consisting of the mixture of non-ionic alkylpolyglucoside surfactant and amphoteric surfactant will constitute no more than 20% w/w of the skin wash composition. Suitably the detergent base will constitute from 5.0 to 15.0% w/w and more suitably from 6.0 to 13.0% w/w of the skin wash composition.

The skin wash compositions of the invention may also contain additional topically acceptable skin conditioning and soothing agents for example in the form of anti-inflammatory agents and vitamins or vitamin derivatives, typically at low concentrations, for example in the range 0.01 to 2.0% w/w of the total composition. Examples of topically acceptable anti-inflammatory agents include allantoin and bisabolol. A preferred vitamin derivative is vitamin E acetate which has anti-inflammatory properties.

Additionally, compositions of the present invention will suitably contain pharmaceutically and cosmetically acceptable additives or excipients conventional in the field of topical medicines and cosmetics, including for example thickeners, moisturisers, re-fatting agents, preservatives, conditioners, chelating agents, buffering agents, colouring agents, fragrances, UV filters and/or emulsifiers. The additives or excipients used in any given composition will be compatible both with each other and with the essential ingredients of the composition such that there is no interaction which would impair the performance of the active ingredients. All additives or excipients must of course be non-toxic and of sufficient purity to render them suitable for human use.

Suitable thickeners include polymeric high molecular weight, non-ionic surfactants consisting of a long chain ($C_{12}$ to $C_{18}$) polyethylene glycol fatty acid or fatty acid residue. Examples include PEG 200 hydrogenated glyceryl palmitate, PEG 55 propylene glycol oleate, PEG 150 distearate and PEG 200 glyceryl tallowate. Suitable low molecular weight thickeners include cocamide DEA, laureth-3 and glyceryl monolaurate. A thickener comprising a polyurethane resin, propylene glycol and water sold under the trade name Acrysol 44 also performs well in detergent based skin wash compositions. A thickener will suitably comprise up to 10.0% w/w of the composition, more suitably from 2.0 to 5.0% w/w. Preferred moisturisers include glycerin, propylene glycol, sorbitol and polyethylene glycol. A moisturiser may comprise up to 15% w/w of the composition, more generally from 2.0 to 6.0% w/w of the composition. Suitable re-fatting agents generally comprising 0.5 to 5.0% w/w of the composition, preferably 0.75 to 2.0% w/w include polyethylene glycol 7 and glyceryl cocoate. Suitable preservatives generally comprising 0.01 to 1.00% w/w of the composition and suitably 0.10 to 0.30% w/w, include phenoxyethanol and methyl dibromo glutaronitrile and mixtures thereof. Suitable conditioners, generally comprising 0.1 to 5.0% w/w of the composition and suitably 1.0 to 3.5% w/w include hydroxycetyl hydroxyethyl dimonium chloride and polyquatemium 39. Suitable chelating agents, generally comprising up to 1.0% w/w of the composition and suitably 0.1 to 0.3% w/w include ethylene diamine tetra-acetic acid (EDTA), hydroethylene diamine triacetic acid (HEEDTA), diethylene triamine penta-acetic acid (DPTA) and cyclohexane diamine tetra-acetic acid (CTDA).

The balance of the composition is typically water plus non-alcohol solvent so as to make up 100% w/w of the composition. In a preferred formulation, water will generally constitute more than 50% w/w of the skin wash composition. Other suitable non-alcohol solvents which may be included to aid formation of a clear solution include glycols such as propylene glycol and polyethylene glycols such as PEG 400 and PEG 40 hydrogenated castor oil/trideceth 9.

The skin wash compositions of the invention may be prepared by methods well known in the art and readily available to the skilled formulator. Generally the triclocarbon is dissolved in non-aqueous solvent, the resulting premix is added to aqueous detergent base together with any additives and the viscosity of the composition is set to the desired level by addition of thickening agent. The present invention extends to a process for preparing a skin wash composition as hereinbefore defined comprising the admixture of a solution of triclocarban in non-aqueous solvent with the detergent base in an aqueous solvent system.

The present invention additionally encompasses the use of a skin wash composition as hereinbefore defined for the manufacture of a medicament for the treatment and/or prophylaxis of acne. The use of compositions of the present invention as hereinbefore defined as a cosmetic treatment for improving the appearance and condition of human skin also forms part of the invention.

The following examples further describe and demonstrate compositions falling within the scope of the invention. For the avoidance of doubt, the examples are provided solely for the purpose of illustration and are not limiting with respect to the scope of the invention.

EXAMPLE 1

Skin Wash Composition Containing 0.10% w/w Triclocarban

A composition comprising the following ingredients was prepared by forming a solution of triclocarban in the non-aqueous solvents, adding the solution to the detergent base and water, which clear solution was then thickened.

| Ingredient | | % w/w |
|---|---|---|
| antibacterial agent | triclocarban | 0.10 |
| detergent base | decyl glucoside | 3.50 |
| | lauryl glucoside | 3.60 |
| | cocamidopropyl betaine | 5.00 |
| thickener | PEG 120 methyl glucoate dioleate | 4.50 |
| pH aduster | citric acid monohydrate | 0.15 |
| solvent | propylene glycol | 5.00 |
| | PEG 400 | 2.50 |
| | PEG 40 hydrogenated castor oil & trideceth 9 | 0.20 |
| | de-ionised water | to 100% |

EXAMPLE 2

Skin Wash Composition Containing 0.10% w/w Triclocarban

The composition of Example 1 was prepared with reduced concentrations of the surfactants making up the detergent base as shown below.

| | | |
|---|---|---|
| detergent base | lauryl glucoside | 2.40 |
| | decyl glucoside | 2.00 |
| | cocamidopropyl betaine | 2.80 |

EXAMPLE 3

Skin Wash Composition Containing 0.15% w/w Triclocarban

The composition of Example 1 was prepared using 0.15% w/w triclocarban.

EXAMPLE 4

Skin Wash Composition Containing 0.10% w/w Triclocarban

The composition of Example 2 containing the additional excipents indicated below was prepared. The resulting product was a clear liquid:

| | |
|---|---|
| conditioner | hydroxycetyl hydroxyethyl dimonium chloride |
| chelating agent | EDTA |
| preservative | phenoxyethanol |
| | methyl dibromo glutaronitrile |
| anti-inflammatory agent | allantoin |
| | vitamin E acetate |
| UV filter | benzophenone |

EXAMPLE 5

Skin Wash Composition Containing 0.15% w/w Triclocarban

The composition of Example 4 was prepared using 0.15% w/w triclocarban.

EXAMPLE 6

Kill Times of Triclocarban Skin Washes Against *P. Acnes* (Strain NCTC 737)

Results are shown in the following table in colony forming units per ml (CFU/ml) remaining after the time point stated and are represented graphically in the appended drawing.

| Example No. | 1 min | 5 min | 10 min | 30 min |
|---|---|---|---|---|
| 1 | $6.35 \times 10^4$ | $1.46 \times 10^4$ | $3.45 \times 10^3$ | $4.0 \times 10^2$ |
| 2 | $9.25 \times 10^4$ | $1.90 \times 10^4$ | $8.75 \times 10^3$ | $6.50 \times 10^2$ |
| 3 | $5.20 \times 10^4$ | $1.21 \times 10^4$ | $3.55 \times 10^3$ | $1.50 \times 10^2$ |
| 4 | $5.10 \times 10^5$ | $1.29 \times 10^4$ | $5.05 \times 10^3$ | $10^2$ |
| 5 | $1.15 \times 10^5$ | $1.53 \times 10^4$ | $1.26 \times 10^4$ | $4.5 \times 10^2$ |

Prior Art (D1–D3) to be Acknowledged in the Description

European Patent Application 422 508 discloses detergent compositions comprising 0.1 to 95% by weight of a saccharide nonionic surfactant and 0.01 to 5% by weight of an antibacterial agent. The detergents are disclosed for use in anti-dandruff and body shampoos.

JP-A-2 152 920 discloses compositions for sterilizing and cleansing skin for use by women during menstruation. The compositions contain 20–70 wt. % synthetic oil and or mineral oil. 1–25 wt. % nonionic surfactant, 0–2 wt. % amphoteric surfactant 0.001–1 wt. % sterilization agent and purified water.

WO 92/18100 discloses liquid cleansing compositions, said to have improved mildness and degerming characteristics. The compositions comprise 0.5–5.75 weight percent of a mild ethoxylated surfactant; 1–40 weight percent of a cosurfactant selected from the group consisting of non-ethoxylated anionic, nonionic, zwitterionic and amphoteric surfactants and mixtures thereof; 0.01–4 weight percent of antibacterial agent; 0.05–5 weight percent of water-soluble cationic polymer and 35–97 weight percent water.

What is claimed is:

1. A skin wash composition comprising from 0.5 to 0.025% w/w of triclocarban and a detergent base consisting of a mixture of a non-ionic alkylpolyglucocide surfactant and an amphoteric surfactant in the absence of an anionic surfactant.

2. A skin wash composition according to claim 1 wherein triclocarban is present at a concentration in the range 0.075 to 0.15% w/w.

3. A skin wash composition according to claim 1 wherein the alkylpolyglucoside surfactant is decyl glucoside, lauryl glucoside or mixtures thereof.

4. A skin wash composition according to claim 1 wherein the alkylpolyglucoside surfactant comprises up to 15% w/w of the composition.

5. A skin wash composition according to claim 4 wherein the alkylpolyglucoside surfactant comprises from 2.0 to 10.0% w/w of the composition.

6. A skin wash composition according to claim 1 wherein the amphoteric surfactant comprises at least one betaine.

7. A skin wash composition according to claim 6 wherein the betaine is cocamidopropyl betaine.

8. A skin wash composition according to claim 1 wherein the amphoteric surfactant comprises up to 10% w/w of the composition.

9. A skin wash composition according to claim 8 wherein the amphoteric surfactant comprises from 2.0 to 8.0% w/w of the composition.

10. A skin wash composition according to claim 1 wherein the detergent base comprises up to 20% w/w of the composition.

11. A skin wash composition according to claim 10 wherein the detergent base comprises from 5.0 to 15.0% w/w of the composition.

12. A skin wash composition according to claim 1 comprising a solvent which is a mixture of water and a non-aqueous solvent.

13. A skin wash composition according to claim 12 wherein the non-aqueous solvent comprises a glycol solvent.

14. A method for the preparation of a composition as defined in claim 12 which method comprises admixture of a solution of triclocarban in non-aqueous solvent with the detergent base in an aqueous solvent system.

15. A method of treatment and/or prophylaxis of acne in a patient which comprises the administration of an anti-acne effective amount of a composition as defined in claim 1 to a patient.

16. A method for improving the appearance and condition of human skin comprising administering an effective amount of a composition defined in claim 1.

* * * * *